US011375952B2

(12) United States Patent
Hatori et al.

(10) Patent No.: US 11,375,952 B2
(45) Date of Patent: Jul. 5, 2022

(54) ADHESIVE HYDROGEL AND MEDICAL ELECTRODE USING THE SAME

(71) Applicant: SEKISUI PLASTICS CO., LTD., Osaka (JP)

(72) Inventors: Takaaki Hatori, Osaka (JP); Takahiko Fujita, Osaka (JP); Kazuhiro Yoshikawa, Osaka (JP)

(73) Assignee: SEKISUI PLASTICS CO., LTD., Osaka (JP)

( * ) Notice: Subject to any disclaimer, the term of this patent is extended or adjusted under 35 U.S.C. 154(b) by 335 days.

(21) Appl. No.: 16/651,700

(22) PCT Filed: Sep. 27, 2018

(86) PCT No.: PCT/JP2018/035865
§ 371 (c)(1),
(2) Date: Mar. 27, 2020

(87) PCT Pub. No.: WO2019/069774
PCT Pub. Date: Apr. 11, 2019

(65) Prior Publication Data

US 2020/0253555 A1 Aug. 13, 2020

(30) Foreign Application Priority Data

Oct. 5, 2017 (JP) ............................ JP2017-195354

(51) Int. Cl.

| | |
|---|---|
| ***A61B 5/00*** | (2006.01) |
| ***C08F 220/56*** | (2006.01) |
| ***C09J 11/04*** | (2006.01) |
| ***C09J 11/06*** | (2006.01) |
| ***C09J 133/26*** | (2006.01) |
| ***A61B 5/288*** | (2021.01) |

(52) U.S. Cl.
CPC ............ *A61B 5/6833* (2013.01); *A61B 5/288* (2021.01); *C08F 220/56* (2013.01); *C09J 11/04* (2013.01); *C09J 11/06* (2013.01); *C09J 133/26* (2013.01); *A61B 2562/0215* (2017.08); *C08F 2800/20* (2013.01); *C08F 2810/20* (2013.01); *C08F 2810/50* (2013.01)

(58) Field of Classification Search
CPC ... A61B 5/6833; A61B 5/288; C08F 222/385; C08F 220/56; C08J 11/04; C09J 11/08
See application file for complete search history.

(56) References Cited

U.S. PATENT DOCUMENTS

| | | | |
|---|---|---|---|
| 4,706,680 A | 11/1987 | Keusch et al. | |
| 5,421,982 A * | 6/1995 | Ikeda | C08F 220/54 528/319 |
| 5,665,477 A | 9/1997 | Meathrel et al. | |
| 5,952,398 A | 9/1999 | Dietz et al. | |
| 6,447,798 B1 | 9/2002 | Munro et al. | |
| 2002/0026005 A1* | 2/2002 | Munro | A61L 15/58 524/514 |
| 2007/0208130 A1* | 9/2007 | Sasahara | A61L 15/585 524/521 |

FOREIGN PATENT DOCUMENTS

| | | |
|---|---|---|
| EP | 0588238 A2 | 9/1993 |
| EP | 1739149 A1 | 3/2005 |
| JP | 2002-521140 A | 7/2002 |
| JP | 2002-521526 A | 7/2002 |
| JP | 5250287 B2 | 7/2013 |
| JP | 2016-67653 A | 5/2016 |
| KR | 20130074065 A | 7/2013 |
| KR | 101419018 B1 | 8/2014 |
| KR | 101419020 B1 | 8/2014 |
| WO | 2009/006397 A2 | 1/2009 |
| WO | 2016/090189 A1 | 6/2016 |

OTHER PUBLICATIONS

International Search Report issued in International Patent Application No. PCT/JP2018/035865, dated Nov. 6, 2018, English translation.
International Preliminary Report on Patentability issued in International Patent Application No. PCT/JP2018/035865, dated Apr. 8, 2020, English translation.
European Search Report, EPO, Application No. 18864728.3, dated Mar. 26, 2021.

* cited by examiner

*Primary Examiner* — Robert C Boyle
(74) *Attorney, Agent, or Firm* — Greenblum & Bernstein, P.L.C.

(57) ABSTRACT

An adhesive hydrogel has low contact resistance against the body surface and excellent conformability and adhesiveness to the body surface, so that noise generation can be reduced. Such adhesive hydrogel enables measurements of weak fetal heart rate signals. The adhesive hydrogel includes a polymer matrix prepared by crosslinking-copolymerization of an acrylamide derivative, which is a nonionic polymerizable monomer including a polymerizable carbon-carbon double bond in a molecule, and polyfunctional (meth)acrylamide, which is a crosslinkable monomer comprising 2 or more polymerizable carbon-carbon double bonds in a molecule, water, a polyvalent alcohol, and an electrolyte salt, wherein a laminate of the adhesive hydrogel with an Ag/AgCl sheet exhibits the impedance of 1Ω to 100Ω at the frequency of 0.1 Hz measured in accordance with the method of ANSI/AAMI EC12:2000, and the dynamic elastic modulus G' at the frequency of 1 Hz measured at 25° C. and dispersed frequencies is $1.0\times10^3$ Pa to $1.0\times10^4$ Pa.

9 Claims, 3 Drawing Sheets

ADHESIVE HYDROGEL AND MEDICAL ELECTRODE USING THE SAME

TECHNICAL FIELD

The present invention relates to an adhesive hydrogel and a medical electrode using the same.

BACKGROUND ART

A medical electrode that is used for electrocardiography or therapy using, for example, low-frequency or medium-frequency electrical stimulation involves the use of a hydrogel adhesive material (an adhesive hydrogel) in a region applied to the body. Such hydrogel is provided between an electrode composed of a conductive material and a skin surface, and examples of a conductive material used include carbon, various metals, and silver-silver chloride (Ag/AgCl).

As an adhesive hydrogel used for a conventional medical electrode, Patent Document 1 discloses a bioadhesive composition, which has: (i) water activity of 0.4 to 0.9; (ii) an elastic modulus at 1 rad/s of 700 to 15,000 Pa; (iii) an elastic modulus at 100 rad/s of 2,000 to 40,000 Pa; (iv) a viscous modulus at 1 rad/s of 400 to 14,000 Pa; and (v) a viscous modulus at 100 rad/s of 1,000 to 35,000 Pa, wherein the viscous modulus is less than the elastic modulus in the frequency range of 1 to 100 rad/s.

Patent Document 2 discloses a bioadhesive composition, which comprises an aqueous plasticized three-dimensional polymeric matrix and a hydrophobic polymer, wherein the concentration of the polymer on the surface of the matrix is greater than its concentration in the matrix.

In recent years, an electrode used for measuring fetal heart rate signals in a pregnant woman has drawn attention among medical electrodes used for measuring heart rate signals, and research and development thereof has been in progress.

PRIOR ART DOCUMENTS

Patent Documents

[Patent Document 1] JP 2002-521140 A
[Patent Document 2] JP 2002-521526 A

SUMMARY OF THE INVENTION

Objects to be Attained by the Invention

The medical electrode used for measuring fetal heart rate signals as described above is applied to the abdominal region, the back region, or other region of a pregnant woman to measure fetal heart rate signals. The fetal heart rate signal intensities, however, are lower than the adult heart rate signal intensities by approximately an order of magnitude. Accordingly, it had been difficult to stably measure fetal heart rate signals. Specifically, the fetal heart rate signal to be measured on the maternal body surface is very weak. For example, it is likely to be influenced by a noise caused by a slight change in the adhesion conditions between the gel and the body surface, and performance of conventional medical electrodes for adults was insufficient. In addition, conventional medical electrodes were not able to stably measure fetal heart rate signals because of wobbling of an electric terminal connected to the apparatus during measurement and a noise caused thereby.

The present invention provides an adhesive hydrogel that enables reduction of generation of noises because of low contact resistance against the body surface and excellent conformability and adhesiveness to the body surface and enables, in particular, measurement of weak fetal heart rate signals. The present invention also provides a medical electrode using such adhesive hydrogel.

In addition, the present invention provides a medical electrode that can be stably adhered to the body surface even when the electric terminal connected to the apparatus would wobble during the measurement, so that generation of noises can be reduced.

Means for Attaining the Objects

The present inventors have conducted concentrated studies and, as a result, they discovered that the objects described above could be attained by identifying a hydrogel composition, adjusting the impedance measured at low frequency within a given range, and adjusting the dynamic elastic modulus G' within a given range. This has led to the completion of the present invention.

In addition, the present inventors discovered that the objects described above could be attained by defining the correlation between the position where a hydrogel is brought into a direct contact with an electrode element and the position where the connector is connected to the electrode element, thereby completing the present invention. Specifically, the present invention is summarized as follows.

(1) An adhesive hydrogel comprising a polymer matrix prepared by crosslinking-copolymerization of an acrylamide derivative, which is a nonionic polymerizable monomer comprising a polymerizable carbon-carbon double bond in a molecule, and polyfunctional (meth) acrylamide, which is a crosslinkable monomer comprising 2 or more polymerizable carbon-carbon double bonds in a molecule, water, a polyvalent alcohol, and an electrolyte salt, wherein a laminate of the adhesive hydrogel with an Ag/AgCl sheet exhibits the impedance of 1Ω to 100Ω at the frequency of 0.1 Hz measured in accordance with the method of ANSI/AAMI EC12:2000, and the dynamic elastic modulus G' at the frequency of 1 Hz measured at 25° C. and dispersed frequencies is $1.0\times10^3$ Pa to $1.0\times10^4$ Pa.

(2) The adhesive hydrogel according to (1), wherein the laminate of the adhesive hydrogel with an Ag/AgCl sheet exhibits the impedance of 1Ω to 70Ω at the frequency of 10 Hz measured in accordance with the method of ANSI/RAMI EC12:2000.

(3) The adhesive hydrogel according to (1) or (2), wherein the dry content is 1% by weight to 15% by weight.

(4) The adhesive hydrogel according to any one of (1) to (3), wherein the adhesive strength is 2 N/20 mm to 8 N/20 mm.

(5) The adhesive hydrogel according to any one of (1) to (4), wherein the moisture content is 10% by weight to 35% by weight and the electrolyte salt content is 4% by weight to 7% by weight.

(6) A medical electrode comprising the adhesive hydrogel according to any one of (1) to (5), an insulating layer superposed on the surface of the adhesive hydrogel, and an electrode element superposed on the surface of the insulating layer, wherein the insulating layer is penetrated in a partial region, and the adhesive hydrogel is brought into direct contact with the electrode element in the partial region, and a connector comprising a cord that transmits signals is connectable to the electrode element.

(7) The medical electrode according to (6), wherein the position in the region where the electrode element is brought into direct contact with the adhesive hydrogel is offset in the extension direction of the cord of the connector.

(8) The medical electrode according to (6) or (7), wherein the connector is immobilized on the medical electrode with the hook-and-loop fasteners.

(9) The medical electrode according to any one of (6) to (8), which is used for measurement of fetal heart rate signals.

This description includes part or all of the content as disclosed in the description and/or drawings of Japanese Patent Application No. 2017-195354, which is a priority document of the present application.

Effects of the Invention

The adhesive hydrogel according to the present invention exhibits low impedance at low frequency and a reduced dynamic elastic modulus G'. When it is applied to the body surface, accordingly, contact resistance is reduced, it is softened, and conformability to the body surface is then improved. When it is used as a medical electrode gel, accordingly, noises are less likely to be generated. Thus, it is particularly preferable for use in measurement of a weak fetal heart rate signal.

With the use of the medical electrode according to the present invention, a noise generated because of wobbling of a terminal connected to the apparatus during measurement can be reduced, and a weak fetal heart rate signal can be stably measured.

EMBODIMENTS FOR IMPLEMENTING THE INVENTION

Figure 1:
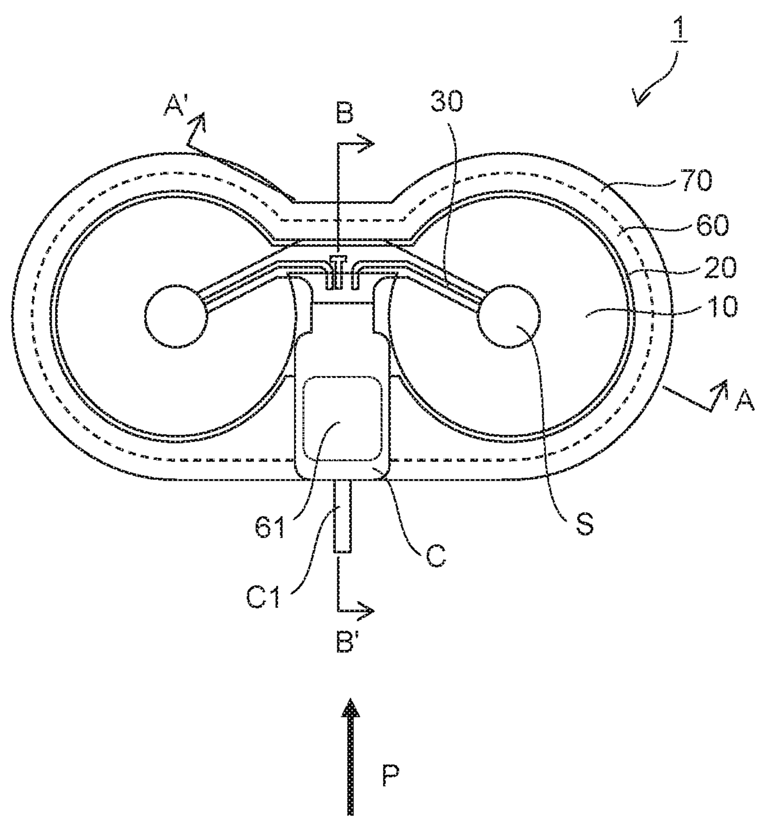
FIG. 1 shows a plane view showing an embodiment of the medical electrode according to the present invention.

Hereafter, the present invention is described in detail with reference to the embodiments.

The adhesive hydrogel according to the present embodiment comprises a polymer matrix prepared by crosslinking-copolymerization of an acrylamide derivative, which is a nonionic polymerizable monomer comprising a polymerizable carbon-carbon double bond in a molecule, and polyfunctional (meth)acrylamide, which is a crosslinkable monomer comprising 2 or more polymerizable carbon-carbon double bonds in a molecule, water, a polyvalent alcohol, and an electrolyte salt. The laminate of the adhesive hydrogel with an Ag/AgCl sheet exhibits the impedance of 1Ω to 100Ω at the frequency of 0.1 Hz measured in accordance with the method of ANSI/AAMI EC12:2000, and the dynamic elastic modulus G' at the frequency of 1 Hz measured at 25° C. and dispersed frequencies is $1.0\times10^3$ Pa to $1.0\times10^4$ Pa.

The adhesive hydrogel according to the present embodiment can be used as a gel member of an electrode for biopotential measurement used for electrocardiogram (ECG), brain wave, nystagmus, or electromyography, an electrode for electrical stimulation used for TENS or low-frequency therapy, a counter electrode plate for electric knife, or a medical electrode, such as an iontophoresis electrode, that is adhered to the body surface. In particular, the adhesive hydrogel according to the present embodiment can be preferably used as a gel member of a medical electrode that is applied to the maternal body during pregnancy to measure weak fetal heart rate signals.

As described above, the impedance at the frequency of 0.1 Hz is preferably regulated within a range of 1Ω to 100Ω, and more preferably 1Ω to 80Ω. Thus, the contact resistance between the adhesive hydrogel and the body surface can be reduced, and noises generated when used as the medical electrode can be reduced. It was found to ensure capturing of fetal heart rate signals, which were significantly weaker than adult heart rate signals.

It is preferable that the impedance at the frequency of 0.1 Hz be 1Ω to 100Ω and the impedance at the frequency of 10 Hz be 1Ω to 70Ω. Thus, noises that could affect heart signal measurements can further be reduced.

The laminate of the adhesive hydrogel with the Ag/AgCl sheet is subjected to measurement of the impedance at the frequency of 0.1 Hz or 10 Hz herein in accordance with the method of ANSI/AAMI EC12:2000. A specific method of measurement is as described below. At the outset, two sets of an analyte adhesive hydrogel to which an Ag/AgCl electrode element is applied are prepared, and sample pieces in which gel regions are in contact with each other are prepared. The signal generator is connected to the oscilloscope through the coaxial cable, and the signal generator is adjusted to realize the output conditions such that the output voltage is 10 V, the output waveform is a sine wave, and the frequency is 0.1 Hz (or 10 Hz). Upon completion of adjustment, coaxial cables are connected to two output termini of the signal generator. A resistor having a resistance value R of 1 MΩ is connected to a coaxial cable, and a silver electrode is further connected to the tip of the coaxial cable. Another silver electrode to be paired with the aforementioned silver electrode is connected to the tip of the other coaxial cable, and both these silver electrodes are adhered to the sample pieces. Also, two coaxial cables are connected to the positive input terminus and the negative input terminus of the oscilloscope, silver electrodes are connected to the tips of the both coaxial cables, and these silver electrodes are adhered to the sample pieces. A voltage is applied to a sample piece from the signal generator, and the voltage $V_2$ lowered by the sample piece is read using an oscilloscope. When the voltage applied from the signal generator is designated as $V_1$, the impedance Z of the sample piece is determined in accordance with the equation (1) below.

$$|Z|=R\times V_2/(V_1-V_2) \quad (1)$$

The voltage $V_2$ read using an oscilloscope, the resistance R=1 MΩ, and the voltage $V_1$=10 V are assigned into the equation (1), so that the impedance Z (Ω) at the frequency of 0.1 Hz or 10 Hz can be measured.

The adhesive hydrogel according to the present embodiment shows the dynamic elastic modulus G' of $1.0\times10^3$ Pa to $1.0\times10^4$ Pa, and more preferably $2.0\times10^3$ Pa to $8.5\times10^3$ Pa, at the frequency of 1 Hz measured at 25° C. and dispersed frequencies. When the dynamic elastic modulus G' is within such range, the adhesive hydrogel is softened, and it sufficiently fits the complicated shape of the body surface when applied to the body surface. Thus, the hydrogel would not be peeled from the body surface even if the body surface configuration is changed, the adhesion between the hydrogel and the body surface can be maintained constant and uniform, and noises that could be generated during the use in the form of a medical electrode can be reduced. When the dynamic elastic modulus G' exceeds $1.0\times10^4$ Pa, the hydrogel loses flexibility, it would not fit the body surface, and the adhesion between the hydrogel and the body surface changes with the elapse of time or due to the position of the hydrogel. Thus, noises generated during the use in the form of a medical electrode are increased, weak fetal heart rate signals cannot be detected, and the dynamic elastic modulus G' exceeding $1.0\times10^4$ Pa is not accordingly suitable. When the dynamic elastic modulus G' is less than $1.0\times10^3$ Pa, shape retaining properties and cohesion of the adhesive hydrogel become insufficient, the hydrogel becomes torn, the impedance varies, and the dynamic elastic modulus G' less than $1.0\times10^3$ Pa thus is not suitable.

The dynamic elastic modulus G' can be measured using, for example, a dynamic viscoelastometer (PHYSICA MCR301, Anton Paar). A measurement sample is prepared by stamping the adhesive hydrogel to form pieces of 25 mmφ and superposing the pieces to a thickness of 0.6 mm.

In the adhesive hydrogel according to the present embodiment, the dry content that is measured as the indicator for the amount of free water is preferably 1% by weight to 15% by weight, more preferably 1% by weight to 13% by weight, and particularly preferably 1% by weight to 10% by weight, relative to the total weight of the hydrogel. The term "free water" used herein refers to the moisture content freely present outside the three-dimensional structure, which is determined by excluding the moisture incorporated into the three-dimensional structure of the hydrogel (i.e., water adsorbed to the three-dimensional structure) from the moisture content of the hydrogel. In the present invention, the dry content that is measured as the indicator for the amount of free water is determined by allowing the adhesive hydrogel to stand at 23° C. and 55% RH for 24 hours, determining the weight thereof lost due to evaporation and dehydration, and calculating the proportion thereof relative to the total weight of the adhesive hydrogel before it was allowed to stand. The present inventors discovered that it would be necessary to regulate the amount of free water as well as the total moisture content including the adsorbed water, so as to lower contact resistance of the adhesive hydrogel. The amount of free water contained in the adhesive hydrogel; i.e., the dry content, can be regulated by primarily increasing/decreasing the amount of a polyvalent alcohol or electrolyte salt. By regulating the dry content within the range of 1% by weight to 10% by weight, contact resistance that is sufficiently low for measurement of fetal heart rate signals can be achieved.

In addition, the adhesive hydrogel according to the present embodiment preferably has the adhesive strength of 2 N/20 mm to 8 N/20 mm, and more preferably 3.5 N/20 mm to 7 N/20 mm. When the adhesive strength is within such range and the adhesive hydrogel is used for the medical electrode, the uniform adhesion conditions between the hydrogel and the body surface can be maintained, noise generation can further be reduced, and such effects can be achieved in combination with satisfactory conformability attained by regulating the dynamic elastic modulus G' within a range of $1.0\times10^3$ Pa to $1.0\times10^4$ Pa. The adhesive strength above is the 90-degree peel resistance of the adhesive hydrogel in accordance with the testing methods of pressure-sensitive adhesive tapes defined by JIS Z 0237:2009. A bakelite board was used as an adherent, and the width of the adhesive frame was 20 mm.

As a nonionic polymerizable monomer constituting an adhesive hydrogel, an acrylamide derivative that is soluble in water and comprises a polymerizable carbon-carbon double bond in a molecule is applicable. When an acrylamide derivative is soluble in water herein, 10 g or more thereof can be dissolved in 100 g of water. When a polymerizable monomer is nonionic, a pH level of an aqueous solution of 1% by weight of such polymerizable monomer, which is in a free acid or base form, is 4 to 9. Examples of nonionic polymerizable monomers include (meth)acrylamide, N,N-dimethyl (meth)acrylamide, N,N-diethyl(meth)acrylamide, and N-isopropyl acrylamide represented by the structure: $CH_2{=}CR^1CONR^2R^3$, wherein $R^1$ represents H or $CH_3$; and $R^2$ and $R^3$ each represent $C_nH_{2n+1}$, wherein n is an integer of 0 to 4. Any of such monomers can be used alone or two or more types thereof can be used in combination. The term "(meth)acrylamide" used herein refers to acrylamide or methacrylamide.

As the crosslinkable monomer, polyfunctional (meth) acrylamide having two or more polymerizable carbon-carbon double bonds in a molecule can be used. Specific examples of such crosslinkable monomers include N,N'-methylenebis(meth)acrylamide and N,N'-ethylenebis(meth) acrylamide. Any of such monomers can be used alone or two or more types thereof can be used in combination.

A polymer matrix is prepared by crosslinking-copolymerization of the nonionic polymerizable monomer and the crosslinkable monomer. The polymer matrix preferably accounts for 10% by weight to 40% by weight, and more preferably 15% by weight to 35% by weight of the entire adhesive hydrogel.

In addition, the proportion of the crosslinkable monomer when preparing the polymer matrix varies depending on types of a nonionic polymerizable monomer and a crosslinkable monomer to be used. In general, the crosslinkable monomer preferably accounts for 0.01% by weight to 0.5% by weight, and more preferably 0.05% by weight to 0.25% by weight of the entire adhesive hydrogel. In order to impart the adhesive hydrogel with morphological stability, the proportion of the crosslinkable monomer is preferably 0.01% by weight or more. In order to impart the adhesive hydrogel with flexibility to retain the adhesive strength, the proportion is preferably 0.5% by weight or less.

The water content in the adhesive hydrogel is preferably 10% by weight to 35% by weight, so as to prevent the gel from undergoing changes in physical properties (swelling or contraction, in particular) with the elapse of time because of moisture absorption or dehydration caused by the surrounding environment.

Examples of polyvalent alcohols that can be used include: diols, such as ethylene glycol, propylene glycol, and butanediol; polyvalent alcohols, such as glycerin, pentaerythritol, and sorbitol; polyvalent alcohol condensates, such as polyethylene glycol, polypropylene glycol, and polyglycerin; and modified polyvalent alcohols, such as polyoxyethylene glycerin. It is preferable to use a polyvalent alcohol that is in a liquid state in the temperature range at which a hydrogel is actually used (e.g., at around 20° C. when used indoors). Examples of polyvalent alcohols that are in a liquid stale include ethylene glycol, propylene glycol, polyethylene glycol, polyglycerin, and glycerin. Any of such polyvalent alcohols can be used alone or two or more types thereof can be used in combination.

The content of the polyvalent alcohol is preferably in the range of 35% by weight to 70% by weight, and more preferably in the range of 40% by weight to 65% by weight, relative to the entire adhesive hydrogel. When the amount of the polyvalent alcohol added is within the range mentioned above, changes in physical properties caused by drying of the resulting hydrogel can be insignificant, and high adhesive strength can be achieved.

Examples of electrolyte salts that can be used include: halides of alkali metals, such as lithium, sodium, and potassium; halides of alkaline earth metals, such as magnesium and calcium; mineral acid salts of carbonic acid, sulfuric acid, and phosphoric acid; inorganic salts; and ammonium salts. In the case of a hydrogel to be applied to the body, neutral to weak acid salts are preferable.

The amount of the electrolyte salt to be added is preferably 4% by weight to 7% by weight, and more preferably 4.5% by weight to 6.5% by weight, relative to the entire adhesive hydrogel. When the amount of the electrolyte salt is excessively small, it is difficult to lower the impedance of the hydrogel. When the amount of the electrolyte salt is excessively large, in contrast, the electrolyte salt cannot be uniformly dissolved in the gel, the salt is likely to precipitate, and the salt is likely to remain undissolved.

When the water content is adjusted to 10% by weight to 35% by weight and the electrolyte salt content is adjusted to 4% by weight to 7% by weight, the amount of free water that would not be captured by the gel increases, and the contact resistance is lowered. This ensures measurements of fetal heart rate signals.

An example of a composition of an adhesive hydrogel constituting the laminate with an Ag/AgCl sheet that exhibits the impedance of 1Ω to 100Ω at a frequency 0.1 Hz measured in accordance with the method of ANSI/AAMI EC12:2000 and the dynamic elastic modulus G' of $1.0\times10^3$ Pa to $1.0\times10^4$ Pa at a frequency of 1 Hz measured at 25° C. and dispersed frequencies is shown below. It should be noted that characteristics of the adhesive hydrogel varies depending on specific types of components, the balance of components, or other additives, in addition to the balance of content or the presence or absence of other additives. Thus, the composition is not limited to the following.

Nonionic polymerizable monomer: 15% by weight to 30% by weight

Crosslinkable monomer: 0.01% by weight to 0.5% by weight

Water: 10% by weight to 35% by weight

Polyvalent alcohol: 35% by weight to 70% by weight

Electrolyte salt: 4% by weight to 7% by weight

According to need, the adhesive hydrogel of the present embodiment may be adequately supplemented with another polymer component such as polyalkylene oxide or poly (meth)acrylic acid, a tackifier, a preservative, a disinfectant, an antifungal agent, a corrosion inhibitor, an antioxidant, an antifoaming agent, a stabilizer, an aroma chemical, a surfactant, a colorant, or another medicinal component, such as an anti-inflammatory agent, vitamin preparation, or skin-lightening agent. The total content of components other than the nonionic polymerizable monomer, the crosslinkable monomer, water, the polyvalent alcohol, and the electrolyte salt is preferably 10% by weight or less in the adhesive hydrogel.

A method for preparing an adhesive hydrogel is not particularly limited, and various means can be employed. For example, a nonionic polymerizable monomer comprising a polymerizable carbon-carbon double bond in a molecule, a crosslinkable monomer comprising 2 or more polymerizable carbon-carbon double bonds in a molecule, water, a polyvalent alcohol, an electrolyte salt, a photopolymerization initiator, and other components are mixed and homogenously dissolved to prepare a gel precursor formulation, and the resulting gel precursor formulation is irradiated with light such as ultraviolet light. Thus, an adhesive hydrogel can be obtained.

Since the gel precursor formulation is a liquid, it may be introduced into, for example, a resin mold and subjected to crosslinking polymerization. Thus, a hydrogel of an arbitrary shape can be prepared. Alternatively, the gel precursor formulation may be introduced into a space between 2 films provided at a given interval and subjected to crosslinking polymerization. Thus, a sheet-form adhesive hydrogel can be obtained.

In general, the gel precursor formulation comprises a photopolymerization initiator. This formulation is irradiated with light such as ultraviolet light to induce crosslinking polymerization. Thus, a hydrogel is obtained. As a photopolymerization initiator, a known initiator, such as an azo-base initiator or an acetophenone-base initiator, can be used. Alternatively, crosslinking polymerization can also be induced via application of radioactive rays, such as electron beams or gamma rays. Among the various polymerization techniques described above, photo-induced polymerization is preferable from the viewpoint of a simple production process, high cost effectiveness, and a possibility of obtaining a gel with stable properties.

Concentration of the photopolymerization initiator is preferably 0.01% by weight or more in an adhesive hydrogel, so as to sufficiently perform the polymerization reaction and reduce the amount of remaining monomers. In order to prevent discoloration (yellowing) or odors caused by the initiator remaining after the reaction, concentration is preferably 1% by weight or less.

The gel precursor formulation can be supplemented with a pH modifier, according to need, for the following reasons. When a pH level is excessively acidic, specifically, an electrode element that is brought into contact with an adhesive hydrogel constituting the medical electrode may undergo corrosion. Examples of pH modifiers include citric acid, sodium citrate, benzoic acid, and sodium benzoate.

When crosslinking polymerization is induced via ultraviolet application, the integral dose of ultraviolet lights applied to the formulation varies depending on the composition of the formulation without particular limitation. In general, the integral dose of 1,000 $mJ/cm^2$ or more is sufficient to satisfactorily promote the polymerization reaction. The integral dose of 2,000 $mJ/cm^2$ or more is more preferable, so that the amount of monomers remaining in the hydrogel can be reduced to 100 ppm or less. While the upper limit of the integral dose is not limited, excessive light application may disadvantageously lead to, for example, an increase in the size of an apparatus, use of excess energy, and the necessity of removal of the heat generated. Thus, the minimum dose is preferable.

Figure 2:
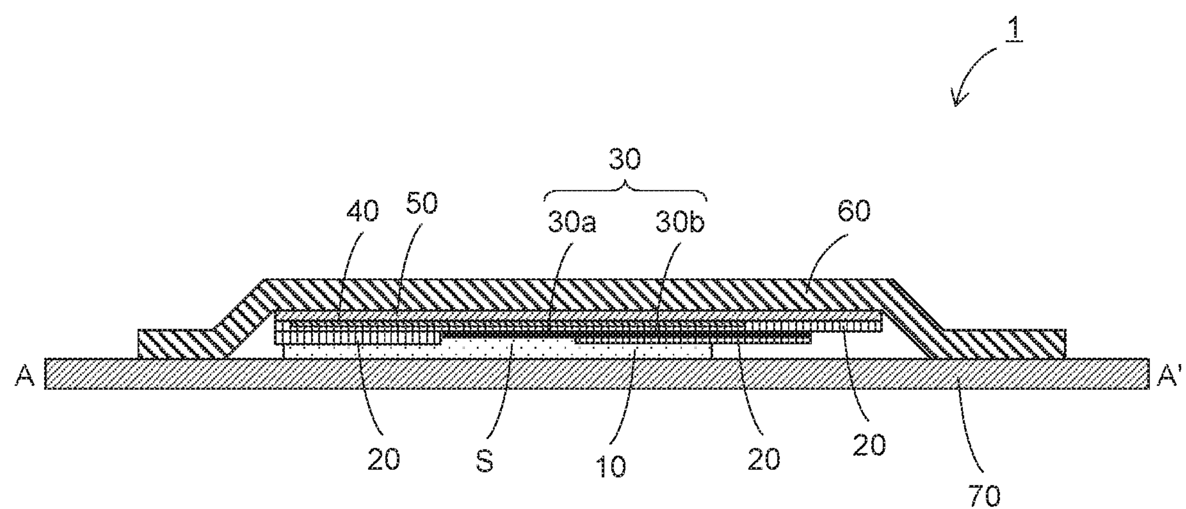
FIG. 2 shows a cross-sectional view along line A-A' of FIG. 1.
Figure 3:
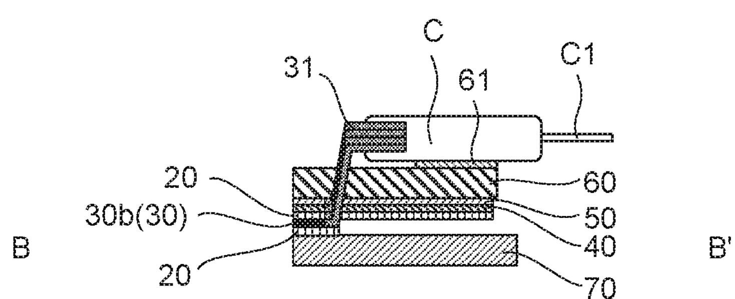
FIG. 3 shows a cross-sectional view along line B-B' of FIG. 1.

Subsequently, a medical electrode using the adhesive hydrogel is described. FIGS. 1 to 3 each show an embodiment of the medical electrode according to the present invention. FIG. 1 is a plane view of the medical electrode, FIG. 2 is a cross-sectional view along line A-A' of FIG. 1, and FIG. 3 is a cross-sectional view along line B-B' of FIG. 1. In FIGS. 2 and 3, each component of the medical electrode 1 is shown to be sufficiently thick for the convenience of description; however, the actual total thickness of the medical electrode 1 is, for example, less than 1 mm to several mm.

As shown in FIGS. 1 to 3, the medical electrode 1 of the present embodiment comprises 2 circular electrodes with a diameter of approximately 1 to 10 cm, and a connector C can be connected to a space between such 2 electrodes. For example, the medical electrode 1 is applied to the body surface to measure heart rate signals. In particular, an adhesive hydrogel that has low contact resistance and excellent conformability and adhesiveness to the body surface is used for a region that is brought into contact with the body surface. Accordingly, the medical electrode 1 can be preferably applied to the maternal body surface during pregnancy to measure weak fetal heart rate signals. The heart rate signals can be measured by connecting a cord C1 extended from the connector C to an electrocardiograph (not shown). The constitution of an electrocardiograph has been known in the past and description thereof is thus omitted herein.

As shown in FIG. 2, the medical electrode 1 at least comprises an adhesive hydrogel 10, an insulating layer 20 superposed on the surface of the adhesive hydrogel 10, and an electrode element 30 superposed on the surface of the insulating layer 20. The electrode element 30 is composed of a sensor 30*a* and a signal wire 30*b*. The insulating layer 20 is penetrated in a partial region (i.e., the region S), and the adhesive hydrogel 10 is brought into direct contact with the sensor 30*a* constituting the electrode element 30 in the region S. The heart rate signals are captured in the region S, the signal is transmitted through the signal wire 30*b* to the conductor 31, and the signal is then inputted into the electrocardiograph through the connector C.

Before the medical electrode 1 is applied to the body surface and used, as shown in FIGS. 1 and 2, the release film 70 is applied to the adhesive hydrogel 10 and the electrode element 30. By coating the adhesive hydrogel 10 with the release film 70, the adhesive hydrogel 10 can be protected and prevented from drying.

According to the present embodiment, the shield layer 40, the resin film 50, and the nonwoven fabric 60 are further superposed on the surface of the electrode element 30 that is opposite from the surface exposed to the body surface through the insulating layer 20.

The shield layer 40 is provided according to need, it has a function of shielding electromagnetic waves, and it can be made of various materials such as a carbon material or a carbon-silver composite paste. By providing the shield layer 40, noises generated during the measurement can further be reduced, and measurement of fetal heart rate signals is ensured.

Any formed and flexible resin film can be used as the resin film 50, and examples thereof include non-conductive films, such as a polyethylene terephthalate film, a polypropylene film, and a polyethylene film, paper, a nonwoven fabric, a foam sheet, and a composite laminate of any thereof. In order to improve appearance of the medical electrode, decorative printing may be provided. It is preferable to adjust thickness of the resin film 50 to approximately 10 μm to 200 μm from the viewpoint of ease of handling, although the thickness is not limited thereto.

The nonwoven fabric 60 and the resin film 50 can be superposed on top of the other through an adhesive layer that is not shown. This adhesive layer is also provided in a peripheral end region (a portion that is not superposed with the resin film 50) of the surface of the nonwoven fabric 60 exposed to the body surface, and the medical electrode 1 can be fixed on the body surface with the aid of the adhesive layer in the peripheral end region. Any adhesive agent can constitute the adhesive layer, provided that it can sufficiently adhere to the skin and skin irritation is insignificant. Specific examples include a rubber-base adhesive agent, a vinyl acetate-base adhesive agent, an ethylene-vinyl acetate-base adhesive agent, a polyvinyl alcohol-base adhesive agent, a polyvinyl acetal-base adhesive agent, an acrylic adhesive agent, a polyamide-base adhesive agent, a polyethylene-base adhesive agent, and a cellulosic adhesive agent.

The adhesive hydrogel 10 may be prepared via crosslinking by coating the surface of the laminate of the electrode element 30 and the insulating layer 20 with a gel precursor formulation. Alternatively, a layer of the adhesive hydrogel 10 may be provided on the release film 70 and the resultant may then be superposed on the laminate of the electrode element 30 and the insulating layer 20.

Thickness of the adhesive hydrogel 10 of the medical electrode 1 is not particularly limited, and it is preferably 0.3 mm to 1.2 mm. When the adhesive hydrogel is excessively thin, temperature may be raised depending on the application of the medical electrode. In addition, the excessively thick adhesive hydrogel 10 would not make any difference in the effects of the medical electrode 1.

The insulating layer 20 that insulates between the adhesive hydrogel 10 and the electrode element 30 in a region other than the region S and materials constituting the same are not particularly limited.

As the sensor 30*a*, for example, a pure silver tape treated with silver/silver chloride can be used without particular limitation. The signal wire 30*b* can be prepared by coating the layer adjacent to the electrode element 30 with a conductive ink containing a metal such as Ag or Ag/AgCl or carbon. Alternatively, a metal foil (e.g., aluminum, stainless steel, or Ag) or a conductive film impregnated with carbon or the like may be superposed on top of the layer adjacent to the electrode element 30.

According to the present embodiment, as shown in FIG. 1, the position of the region S where the sensor 30*a* of the electrode element 30 is brought into direct contact with the adhesive hydrogel 10 is offset in the extension direction (indicated by an arrow P) of the cord C1 of the connector C. When the position of the region S is "offset," it is not on the line extended from the line indicated by the arrow P, but it deviates therefrom. When the cord C1 or the connector C swing and wobble during the use of the medical electrode 1, the adhesion conditions between the region S serving as a sensor and the body would not be influenced, and noises are less likely to be generated.

According to the present embodiment, as shown in FIG. 1 and FIG. 3, hook-and-loop fasteners 61 are provided on the lower surface of the connector C and on the upper surface of the nonwoven fabric 60. By fixing the connector C on the medical electrode 1 with the hook-and-loop fasteners 61, the connector C would not wobble, and noise generation would further be suppressed. As the hook-and-loop fasteners 61, for example, well-known fasteners comprising a pair of sheet materials that are superposed on top of each other, numerous tiny loops on the surface of a sheet material, and numerous hooks to be engaged with the loops on the surface of the other sheet material can be used.

While the embodiments above describe the case wherein the medical electrode 1 comprises 2 circular electrodes, the electrode is not limited thereto. For example, a plane layout of the electrode can be arbitrarily changed by changing the number of circular electrodes to 1 to 3. When the medical electrode 1 is applied to the maternal body surface so as to measure the fetal heart rate signals, a plurality of medical electrodes 1 can be applied to the abdominal region and the back region. When the positions to be applied are determined depending on types of the medical electrode 1, each of a plurality of medical electrodes 1 can be used in appropriate combination with a relevant connector C to be connected therewith by, for example, marking the hook-and-loop fasteners 61 on the nonwoven fabric 60 and the connectors C to be fixed thereon with the same color. In addition, it should be noted that the present invention is not limited by the embodiments described above, and each component can be adequately omitted or modified or other components can be added within the scope of the invention.

EXAMPLES

Hereafter, the present invention is described in greater detail with reference to the examples and the comparative examples, although the present invention is not limited to these examples.

Example 1

Acrylamide (AAM) in an amount of 19.0% by weight (relative to the whole adhesive hydrogel designated as 100% by weight; the same applies herein below) as a nonionic polymerizable monomer, 0.027% by weight of N,N-methylenebis acrylamide as a crosslinkable monomer, 28.0% by weight of water, 46.243% by weight of glycerin as a polyvalent alcohol, 5.6% by weight of sodium chloride as an electrolyte salt, and 1.0% by weight of an acrylic acid-methacrylic acid (7:3) copolymer as a tackifier were mixed, and the mixture was agitated to dissolve the contents. Thus, a gel precursor formulation was prepared. Subsequently, 0.13% by weight of 1-[4-(2-hydroxyethoxy)-phenyl]-2-hydroxy-2-methyl-1-propan-1-one was added as a photopolymerization initiator to the gel precursor formulation, and the mixture was further agitated to dissolve the contents. Subsequently, the gel precursor formulation was introduced into a poly carbonate mold (130 mm×130 mm; thickness: 1.0 mm) on a silicon-treated biaxially stretched polyester film (thickness: 100 μm) on the glass, a silicon-treated biaxially stretched polyester film (thickness: 38 μm) was superposed on the mold while avoiding air bubbles, and the thickness of the resultant was made uniform by superposing quartz glass thereon. The resultant was irradiated with ultraviolet light with the peak intensity of 50 mW/cm$^2$ using an ultraviolet lamp for 60 seconds, and the resultant was removed from the mold to obtain a sheet-form adhesive hydrogel of Example 1.

Example 2

Acrylamide (18.0% by weight) as a nonionic polymerizable monomer, 0.022% by weight of N,N-methylenebis acrylamide as a crosslinkable monomer, 28.0% by weight of water, 48.098% by weight of glycerin as a polyvalent alcohol, 5.0% by weight of sodium chloride as an electrolyte salt, 0.5% by weight of an acrylic acid-methacrylic acid (7:3) copolymer as a tackifier, and 0.25% by weight of an acrylic acid-acrylamidomethylpropanesulfonic acid (7:3) copolymer were mixed, and the mixture was agitated to dissolve the contents. Thus, a gel precursor formulation was prepared. Subsequently, 0.13% by weight of 1-[4-(2-hydroxyethoxy)-phenyl]-2-hydroxy-2-methyl-1-propan-1-one was added as a photopolymerization initiator to the gel precursor formulation, and the mixture was further agitated to dissolve the contents. Thereafter, the adhesive hydrogel of Example 2 was obtained in the same manner as in Example 1.

Example 3

Acrylamide (18.0% by weight) as a nonionic polymerizable monomer, 0.018% by weight of N,N-methylenebis acrylamide as a crosslinkable monomer, 28.0% by weight of water, 47.252% by weight of glycerin as a polyvalent alcohol, 5.6% by weight of sodium chloride as an electrolyte salt, and 1.0% by weight of an acrylic acid-methacrylic acid (7:3) copolymer as a tackifier were mixed, and the mixture was agitated to prepare a gel precursor formulation. Subsequently, 0.13% by weight of 1-[4-(2-hydroxyethoxy)-phenyl]-2-hydroxy-2-methyl-1-propan-1-one was added as a photopolymerization initiator to the gel precursor formulation, and the mixture was further agitated to dissolve the contents. Thereafter, the adhesive hydrogel of Example 3 was obtained in the same manner as in Example 1.

Example 4

N,N-Dimethylacrylamide (DMAA) (20.0% by weight) as a nonionic polymerizable monomer, 0.034% by weight of N,N-methylenebis acrylamide as a crosslinkable monomer, 24.0% by weight of water, 51.836% by weight of glycerin as a polyvalent alcohol, and 4.0% by weight of sodium chloride as an electrolyte salt were mixed, and the mixture was agitated to prepare a gel precursor formulation. Subsequently, 0.13% by weight of 1-[4-(2-hydroxyethoxy)-phenyl]-2-hydroxy-2-methyl-1-propan-1-one was added as a photopolymerization initiator to the gel precursor formulation, and the mixture was further agitated to dissolve the contents. Thereafter, the adhesive hydrogel of Example 4 was obtained in the same manner as in Example 1.

Example 5

Acrylamide (19.0% by weight) as a nonionic polymerizable monomer, 0.027% by weight of N,N-methylenebis acrylamide as a crosslinkable monomer, 28.0% by weight of water, 47.243% by weight of polyglycerin as a polyvalent alcohol, and 5.6% by weight of sodium chloride as an electrolyte salt were mixed, and the mixture was agitated to prepare a gel precursor formulation. Subsequently, 0.13% by weight of 1-[4-(2-hydroxyethoxy)-phenyl]-2-hydroxy-2-methyl-1-propan-1-one was added as a photopolymerization initiator to the gel precursor formulation, and the mixture was further agitated to dissolve the contents. Thereafter, the adhesive hydrogel of Example 5 was obtained in the same manner as in Example 1.

Example 6

Acrylamide (19.0% by weight) as a nonionic polymerizable monomer, 0.027% by weight of N,N-methylenebis acrylamide as a crosslinkable monomer, 33.0% by weight of water, 41.843% by weight of glycerin as a polyvalent alcohol, and 6.0% by weight of sodium chloride as an electrolyte salt were mixed, and the mixture was agitated to prepare a gel precursor formulation. Subsequently, 0.13% by weight of 1-[4-(2-hydroxyethoxy)-phenyl]-2-hydroxy-2-methyl-1-propan-1-one was added as a photopolymerization initiator to the gel precursor formulation, and the mixture was further agitated to dissolve the contents. Thereafter, the adhesive hydrogel of Example 6 was obtained in the same manner as in Example 1.

Example 7

Acrylamide (15.0% by weight) as a nonionic polymerizable monomer, 0.015% by weight of N,N-methylenebis acrylamide as a crosslinkable monomer, 28.0% by weight of water, 51.255% by weight of glycerin as a polyvalent alcohol, and 5.6% by weight of sodium chloride as an electrolyte salt were mixed, and the mixture was agitated to prepare a gel precursor formulation. Subsequently, 0.13% by weight of 1-[4-(2-hydroxyethoxy)-phenyl]-2-hydroxy-2-methyl-1-propan-1-one was added as a photopolymerization initiator to the gel precursor formulation, and the mixture was further agitated to dissolve the contents. Thereafter, the adhesive hydrogel of Example 7 was obtained in the same manner as in Example 1.

Comparative Example 1

N,N-Dimethylacrylamide (DMAA) (20.0% by weight) as a nonionic polymerizable monomer, 0.034% by weight of N,N-methylenebis acrylamide as a crosslinkable monomer, 17.0% by weight of water, 58.836% by weight of polyglycerin as a polyvalent alcohol, and 4.0% by weight of sodium chloride as an electrolyte salt were mixed, and the mixture was agitated to prepare a gel precursor formulation. Subsequently, 0.13% by weight of 1-[4-(2-hydroxyethoxy)-phenyl]-2-hydroxy-2-methyl-1-propan-1-one was added as photopolymerization initiator to the gel precursor formulation, and the mixture was further agitated to dissolve the contents. Thereafter, the adhesive hydrogel of Comparative Example 1 was obtained in the same manner as in Example 1.

Comparative Example 2

Acrylamide (17.0% by weight) as a nonionic polymerizable monomer, 0.030% by weight of N,N-methylenebis acrylamide as a crosslinkable monomer, 23.4% by weight of water, 55.950% by weight of glycerin as a polyvalent alcohol, 1.9% by weight of sodium chloride as an electrolyte salt, 1.1% by weight of an acrylic acid-methacrylic acid (7:3) copolymer as a tackifier, and 0.5% by weight of an acrylic acid-acrylamidomethylpropanesulfonic acid (7:3) copolymer were mixed, and the mixture was agitated to prepare a gel precursor formulation. Subsequently, 0.12% by weight of 1-[4-(2-hydroxyethoxy)-phenyl]-2-hydroxy-2-methyl-1-propan-1-one was added as a photopolymerization initiator to the gel precursor formulation, and the mixture was further agitated to dissolve the contents. Thereafter, the adhesive hydrogel of Comparative Example 2 was obtained in the same manner as in Example 1.

Comparative Example 3

Acrylamide (24.0% by weight) as a nonionic polymerizable monomer, 0.048% by weight of N,N'-methylenebis acrylamide as a crosslinkable monomer, 30.6% by weight of water, 39.292% by weight of glycerin as a polyvalent alcohol, 5.6% by weight of sodium chloride as an electrolyte salt, and 0.36% by weight of polyvinyl alcohol with a viscosity average degree of polymerization of 1800 and a degree of saponification of 88% were mixed, and the mixture was agitated to dissolve the contents. Thus, a gel precursor formulation was prepared. Subsequently, 0.10% by weight of 1-hydroxy-cyclohexyl phenyl ketone (tradename: Irgacure 184, BASF) was added as a photopolymerization initiator to the gel precursor formulation, and the mixture was further agitated to dissolve the contents. Thereafter, the adhesive hydrogel of Comparative Example 3 was obtained in the same manner as in Example 1.

Comparative Example 4

Acrylamide (24.0% by weight) as a nonionic polymerizable monomer, 0.048% by weight of N,N'-methylenebis acrylamide as a crosslinkable monomer, 30.6% by weight of water, 44.892% by weight of glycerin as a polyvalent alcohol, and 0.36% by weight of polyvinyl alcohol with a viscosity average degree of polymerization of 1800 and a degree of saponification of 88% were mixed, and the mixture was agitated to dissolve the contents. Thus, a gel precursor formulation was prepared. Subsequently, 0.10% by weight of 1-hydroxy-cyclohexyl phenyl ketone (tradename: Irgacure 184, BASF) was added as a photopolymerization initiator to the gel precursor formulation, and the mixture was further agitated to dissolve the contents. Thereafter, the adhesive hydrogel of Comparative Example 4 was obtained in the same manner as in Example 1.

Comparative Example 5

The adhesive hydrogel of Comparative Example 5 was obtained in the same manner as in Example 1 except that the amount of N,N-methylenebis acrylamide as a crosslinkable monomer and that of glycerin as a polyvalent alcohol were changed to 0.11% by weight and 46.160% by weight, respectively.

Comparative Example 6

The adhesive hydrogel of Comparative Example 6 was obtained in the same manner as in Example 1 except that the amount of sodium chloride as an electrolyte salt and that of glycerin as a polyvalent alcohol were changed to 0% by weight and 51.843% by weight, respectively.

[Measurement of Impedance]

The laminates of each of the adhesive hydrogels according to Examples 1 to 7 and Comparative Examples 1 to 6 with an Ag/AgCl sheet were subjected to measurements of the impedance at a frequency of 0.1 Hz and 10 Hz in accordance with the method of ANSI/AAMI EC12:2000. The results of measurements are shown in Table 1 and Table 2.

[Measurement of Dynamic Elastic Modulus G']

The dynamic elastic modulus G' of the adhesive hydrogels according to Examples 1 to 7 and Comparative Examples 1 to 6 was determined at a frequency of 1 Hz measured at 25° C. and dispersed frequencies using the dynamic viscoelastometer (PHYSICA MCR301, Anton Paar). The results of measurements are shown in Table 1 and Table 2.

[Measurement of Content]

The adhesive hydrogels according to Examples 1 to 7 and Comparative Examples 1 to 6 were allowed to stand at 23° C. and 55% RH for 24 hours, and the dry content as the indicator for the amount of free water in the adhesive hydrogel was determined based on the weight lost due to evaporation and dehydration. The results of measurements are shown in Table 1 and Table 2.

[Measurement of Adhesive Strength]

The 90-degree peel resistance of the adhesive hydrogels according to Examples 1 to 7 and Comparative Examples 1 to 6 was measured in accordance with the testing methods of pressure-sensitive adhesive tapes defined by JIS Z 0237:2009. A bakelite board was used as an adherent, and the width of the adhesive frame was 20 mm. The results of measurements are shown in Table 1 and Table 2.

[Measurement of Noise Level]

Signal generators were connected to the adhesive hydrogels according to Examples 1 to 7 and Comparative Examples 1 to 6 in accordance with the method of ANSI/AAMI EC12:2000 and adjusted to output a voltage of 10 V and a sine waveform with a frequency of 0.1 Hz. Resistance of 10 MΩ was connected to the cable (resistance of 10 MΩ was employed herein while that of 1 MΩ was employed in accordance with ANSI/AAMI EC 12:2000), and the voltage waveform was read using an oscilloscope (TDS 3014, Tektronix). In the sine wave read by the oscilloscope, a point at which the line width of the signal at the positive (top) or negative (bottom) peak would reach the maximum among continuing positive and negative peaks was selected, and the noise level (unit: μV) was defined based on the signal line width along the Y axis (the voltage) of the sine wave at the selected point. The results of measurements are shown in Table 1 and Table 2.

[Results of Measurements]

As shown in Table 1 and Table 2, the adhesive hydrogels according to Examples 1 to 7 exhibiting the impedance of 1Ω to 100Ω at the frequency of 0.1 Hz and the dynamic elastic modulus G' of $1.0\times10^3$ Pa to $1.0\times10^4$ Pa were found to generate noises lower than those generated by the adhesive hydrogels according to Comparative Examples. This indicates that the adhesive hydrogels according to Examples 1 to 7 enable measurements while suppressing noises at a very low frequency band of 0.1 Hz.

TABLE 1

| | Ex. 1 | Ex. 2 | Ex. 3 | Ex. 4 | Ex. 5 | Ex. 6 | Ex. 7 |
|---|---|---|---|---|---|---|---|
| Nonionic polymerizable monomer (AAM) (wt %) | 19.0 | 18.0 | 18.0 | — | 19.0 | 19.0 | 15.0 |
| Nonionic polymerizable monomer (DMAA) (wt %) | — | — | — | 20.0 | — | — | — |
| Crosslinkable monomer (wt %) | 0.027 | 0.022 | 0.018 | 0.034 | 0.027 | 0.027 | 0.015 |
| Water (wt %) | 28.0 | 28.0 | 28.0 | 24.0 | 28.0 | 33.0 | 28.0 |
| Polyvalent alcohol (glycerin) (wt %) | 46.243 | 48.098 | 47.252 | 51.836 | — | 41.843 | 51.255 |
| Polyvalent alcohol (polyglycerin) (wt %) | — | — | — | — | 47.243 | — | — |
| Electrolyte salt (wt %) | 5.6 | 5.0 | 5.6 | 4.0 | 5.6 | 6.0 | 5.6 |
| Polyvinyl alcohol (wt %) | — | — | — | — | — | — | — |
| Acrylic acid-methacrylic acid copolymer (wt %) | 1.0 | 0.5 | 1.0 | — | — | — | — |
| Acrylic acid-acrylamidomethylpropanesulfonic acid copolymer (wt %) | — | 0.25 | — | — | — | — | — |
| Photopolymerization initiator (wt %) | 0.13 | 0.13 | 0.13 | 0.13 | 0.13 | 0.13 | 0.13 |
| Impedance at 10 Hz (Ω) | 34.6 | 32.2 | 35.4 | 38.4 | 34.4 | 24.4 | 27.2 |
| Impedance at 0.1 Hz (Ω) | 68.4 | 62 | 59.6 | 98.0 | 68.0 | 52.0 | 66.0 |
| Dryness factor (wt %) | 8.41 | 5.32 | 2.09 | 4.48 | 12.1 | 9.69 | 7.2 |
| Dynamic elastic modulus G' (Pa) | 7993 | 3182 | 6311 | 2569 | 6928 | 5654 | 1826 |
| Adhesion strength (N/20 mm) | 5.0 | 4.4 | 6.4 | 2.2 | 6.5 | 2.6 | 3.2 |
| Noise level (μV) | 24 | 30 | 30 | 33 | 26 | 20 | 22 |

* Content of each component is relative to the entire adhesive hydrogel.

TABLE 2

| | Comp. Ex. 1 | Comp. Ex. 2 | Comp. Ex. 3 | Comp. Ex. 4 | Comp. Ex. 5 | Comp. Ex. 6 |
|---|---|---|---|---|---|---|
| Nonionic polymerizable monomer (AAM) (wt %) | — | 17.0 | 24.0 | 24.0 | 19.0 | 19.0 |
| Nonionic polymerizable monomer (DMAA) (wt %) | 20.0 | — | — | — | — | — |
| Crosslinkable monomer (wt %) | 0.034 | 0.030 | 0.048 | 0.048 | 0.11 | 0.027 |
| Water (wt %) | 17.0 | 23.4 | 30.6 | 30.6 | 28.0 | 28.0 |
| Polyvalent alcohol (glycerin) (wt %) | — | 55.950 | 39.292 | 44.892 | 46.160 | 51.843 |
| Polyvalent alcohol (polyglycerin) (wt %) | 58.836 | — | — | — | — | — |
| Electrolyte salt (wt %) | 4.0 | 1.9 | 5.6 | — | 5.6 | — |
| Polyvinyl alcohol (wt %) | — | — | 0.36 | 0.36 | — | — |
| Acrylic acid-methacrylic acid copolymer (wt %) | — | 1.1 | — | — | 1.0 | 1.0 |
| Acrylic acid-acrylamidomethylpropanesulfonic acid copolymer (wt %) | — | 0.5 | — | — | — | — |
| Photopolymerization initiator (wt %) | 0.13 | 0.12 | 0.10 | 0.10 | 0.13 | 0.13 |
| Impedance at 10 Hz (Ω) | 166 | 74.4 | 41 | 4320 | 42.6 | 694 |
| Impedance at 0.1 Hz (Ω) | 106 | 135 | 58.4 | 3900 | 65.6 | 1270 |
| Dryness factor (wt %) | 1.68 | 1.36 | 7.27 | 10.01 | 6.11 | 8.35 |
| Dynamic elastic modulus G' (Pa) | 4833 | 5488 | 27264 | 21822 | 13741 | 7286 |
| Adhesion strength (N/20 mm) | 7.9 | 4.7 | 1.7 | 1.8 | 1.9 | 5.2 |
| Noise level (μV) | 92 | 50 | 36 | 3200 | 35 | 340 |

* Content of each component is relative to the entire adhesive hydrogel.

DESCRIPTION OF REFERENCES

1: Medical electrode
10: Adhesive hydrogel
20: Insulating layer
30: Electrode element
30*a*: Sensor
30*b*: Signal line
31: Conductor
40: Shield layer
50: Resin film
60: Nonwoven fabric
61: Hook-and-loop fasteners
70: Release film
C: Connector
C1: Cord
S: Region All publications, patents, and patent applications cited herein are incorporated herein by reference in their entirety.

The invention claimed is:

1. An adhesive hydrogel comprising a polymer matrix prepared by crosslinking-copolymerization of an acrylamide derivative, which is a nonionic polymerizable monomer comprising a polymerizable carbon-carbon double bond in a molecule, and polyfunctional (meth)acrylamide, which is a crosslinkable monomer comprising 2 or more polymerizable carbon-carbon double bonds in a molecule, water, a polyvalent alcohol, and an electrolyte salt, wherein a laminate of the adhesive hydrogel with an Ag/AgCl sheet exhibits the impedance of 1Ω to 100Ω at the frequency of 0.1 Hz measured in accordance with the method of ANSI/AAMI EC12:2000, and the dynamic elastic modulus G' at the frequency of 1 Hz measured at 25° C. and dispersed frequencies is $1.0\times10^3$ Pa to $1.0\times10^4$ Pa.

2. The adhesive hydrogel according to claim 1, wherein the laminate of the adhesive hydrogel with an Ag/AgCl sheet exhibits the impedance of 1Ω to 70Ω at the frequency of 10 Hz measured in accordance with the method of ANSI/AAMI EC12:2000.

3. The adhesive hydrogel according to claim 1, wherein the dry content is 1% by weight to 15% by weight.

4. The adhesive hydrogel according to claim 1, wherein the adhesive strength is 2 N/20 mm to 8 N/20 mm.

5. The adhesive hydrogel according to claim 1, wherein the moisture content is 10% by weight to 35% by weight and the electrolyte salt content is 4% by weight to 7% by weight.

6. A medical electrode comprising the adhesive hydrogel according to claim 1, an insulating layer superposed on the surface of the adhesive hydrogel, and an electrode element superposed on the surface of the insulating layer, wherein the insulating layer is penetrated in a partial region, and the adhesive hydrogel is brought into direct contact with the electrode element in the partial region, and a connector comprising a cord that transmits signals is connectable to the electrode element.

7. The medical electrode according to claim 6, wherein the position in the region where the electrode element is brought into direct contact with the adhesive hydrogel is offset in the extension direction of the cord of the connector.

8. The medical electrode according to claim 6, wherein the connector is immobilized on the medical electrode with the hook-and-loop fasteners.

9. The medical electrode according to claim 6, which is used for measurement of fetal heart rate signals.

* * * * *